(12) United States Patent
Jensen et al.

(10) Patent No.: US 11,436,908 B2
(45) Date of Patent: Sep. 6, 2022

(54) INTELLIGENT INERT MEASUREMENT MODE

(71) Applicant: Honeywell International Inc., Charlotte, NC (US)

(72) Inventors: Jesper Jensen, Morris Plains, NJ (US); Jacob Thomas Spector, Morris Plains, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 17/497,271

(22) Filed: Oct. 8, 2021

(65) Prior Publication Data

US 2022/0028242 A1 Jan. 27, 2022

Related U.S. Application Data

(63) Continuation of application No. 16/464,926, filed as application No. PCT/US2016/064162 on Nov. 30, 2016, now Pat. No. 11,170,629.

(51) Int. Cl.
*G08B 21/18* (2006.01)
*G01N 33/00* (2006.01)
(Continued)

(52) U.S. Cl.
CPC ....... *G08B 21/182* (2013.01); *G01N 33/0065* (2013.01); *G08B 17/10* (2013.01);
(Continued)

(58) Field of Classification Search
CPC ...... G08B 21/182; G08B 17/10; G08B 21/16; G08B 29/02; G08B 21/12; G01N 33/0065
See application file for complete search history.

(56) References Cited

U.S. PATENT DOCUMENTS 4,352,087 A * 9/1982 Wittmaier ............... G08B 17/10
340/634
4,868,546 A * 9/1989 Dumbeck ............ G08B 17/117
250/DIG. 2
(Continued)

FOREIGN PATENT DOCUMENTS

GB 2527758 A 10/2005

OTHER PUBLICATIONS

Communication Pursuant to Rule 161(1) and 162 for European Application No. 16813263.7 dated Jul. 9, 2019, 5 pages.
(Continued)

*Primary Examiner* — Ojiako K Nwugo
(74) *Attorney, Agent, or Firm* — Alston & Bird LLP

(57) ABSTRACT

Embodiments relate generally to systems and methods for gas detection. A method may comprise operating a gas detector with a first alarm setting comprising a first predefined threshold; receiving sensed data of oxygen content in the ambient air; when the sensed data is below the first predefined threshold, activating an alarm; generating an acknowledgement request asking if the gas detector has entered an inert work zone; receiving a response from the user acknowledging that the gas detector has entered an inert work zone; deactivating the alarm; changing the alarm settings of the gas detector to a second alarm setting comprising a second predefined threshold; continuing to receive sensed data of oxygen content in the ambient air; when the sensed data is above the second predefined threshold, activating an alarm; and generating an acknowledgement request for the user asking if the gas detector has entered a normal operation work zone.

20 Claims, 1 Drawing Sheet

(51) Int. Cl.
  *G08B 17/10* (2006.01)
  *G08B 29/02* (2006.01)
  *G08B 21/16* (2006.01)
  *G08B 21/22* (2006.01)

(52) U.S. Cl.
  CPC ............ *G08B 21/16* (2013.01); *G08B 29/02* (2013.01); *G08B 21/22* (2013.01)

(56) References Cited

U.S. PATENT DOCUMENTS

| | | | |
|---|---|---|---|
| 9,612,195 | B1 | 4/2017 | Friedman |
| 9,964,530 | B2 | 5/2018 | Baldaccini |
| 9,978,251 | B2 | 5/2018 | Gonia et al. |
| 10,847,011 | B2 | 11/2020 | Delgado |
| 2012/0068842 | A1 | 3/2012 | Piccolo, III |
| 2012/0280818 | A1 | 11/2012 | Johnson et al. |
| 2013/0024563 | A1 | 1/2013 | Torigoe et al. |
| 2014/0005505 | A1* | 1/2014 | Peyser ............... A61B 5/7221 600/347 |
| 2016/0127862 | A1 | 5/2016 | Beattie, Jr. |
| 2016/0334378 | A1 | 11/2016 | Maddila et al. |
| 2017/0160248 | A1* | 6/2017 | Roizin ............... G01N 27/74 |

OTHER PUBLICATIONS

Decision to grant a European patent dated Dec. 10, 2020 for EP Application No. 16813263.7, 2 pages.
Examination Report for Australian Application No. 2016430856, dated Nov. 20, 2019, 3 pages.
Extended European Search Report issued in European Application No. 20202788.4 dated Feb. 8, 2021, 7 pages.
Intention to Grant issued in European Application No. 16813263.7 dated Jul. 29, 2020, 5 pages.
International Search Report and Written Opinion for International Application No. PCT/US2016/064162 dated Jul. 18, 2017.
Non-Final Rejection dated Apr. 21, 2021 for U.S. Appl. No. 16/464,926.
Notice of Acceptance for Australian Application No. 2016430856, dated Mar. 2, 2020, 3 pages.
Notice of Acceptance issued in Australian Application No. 2020203600 dated Apr. 1, 2021, 3 pages.
Notice of Allowance received for U.S. Appl. No. 16/464,926, dated Jul. 16, 2021, 8 pages.
Communication about intention to grant a European patent received for European Application No. 20202788.4, dated Jan. 25, 2022, 6 pages.

* cited by examiner

INTELLIGENT INERT MEASUREMENT MODE

CROSS-REFERENCE TO RELATED APPLICATIONS

This application is a continuation of U.S. Non-Provisional patent application Ser. No. 16/464,926, filed May 29, 2019 and entitled "Intelligent Inert Measurement Mode," which is a National Stage Entry of International Patent Application Serial Number PCT/US2016/064162, filed Nov. 30, 2016 and entitled "Intelligent Inert Measurement Mode," the entire disclosures of each of which are hereby incorporated herein by reference in their entireties for all purposes.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be carried and/or worn by workers in many different work environments. Gas detectors may be equipped with one or more gas sensors configured to detect particular gasses, such as ambient air gases, hazardous gases, oxygen, nitrogen, carbon dioxide, carbon monoxide, volatile organic compounds (VOCs), etc. The gas detectors may also be configured to alarm based on the presence, or lack of, a particular gas.

SUMMARY

In an embodiment, a method for gas detection may comprise operating a gas detector with a first alarm setting comprising a first predefined threshold; receiving sensed data containing the current oxygen content in the ambient air; when the sensed data is below the first predefined threshold, activating an alarm; and generating an acknowledgement request for the user asking if the gas detector has entered an inert work zone.

In an embodiment, a gas detector may comprise a user interface configured to communicate information to a user, and to receive information from a user; an alarm; a sensor configured to detect the oxygen content in the ambient air around the gas detector; a processor configured to operate the gas detector with a first alarm setting comprising a first predefined threshold; receive sensed data, from the sensor, containing the current oxygen content in the ambient air; when the sensed data is below the first predefined threshold, activate the alarm; and generate an acknowledgement request for the user asking if the gas detector has entered an inert work zone.

In an embodiment, a method for gas detection may comprise operating a gas detector with a first alarm setting comprising a first predefined threshold, wherein the first alarm setting indicates that the alarm is activated when the oxygen content is below the first predefined threshold; receiving sensed data containing the current oxygen content in the ambient air; when the sensed data is below the first predefined threshold, activating an alarm; generating an acknowledgement request for the user asking if the gas detector has entered an inert work zone; receiving a response from the user acknowledging that the gas detector has entered an inert work zone; deactivating the alarm; changing the alarm settings of the gas detector to a second alarm setting comprising a second predefined threshold, wherein the second alarm setting indicates that the alarm is activated when the oxygen content is above the second predefined threshold; continuing to receive sensed data containing the current oxygen content in the ambient air; when the sensed data is above the second predefined threshold, activating an alarm; and generating an acknowledgement request for the user asking if the gas detector has entered a normal operation work zone.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
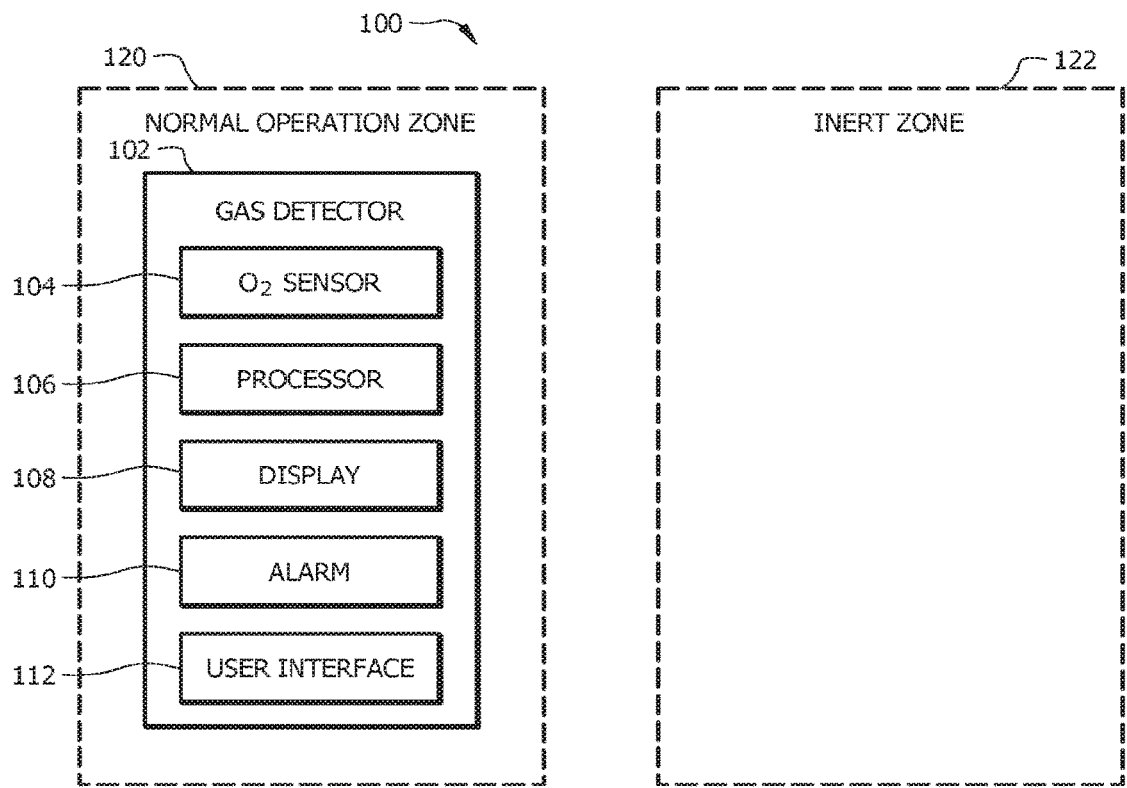
FIG. 1 illustrates a gas detector in use in a normal operation zone according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for gas detection in normal work zones and inert work zones. In normal work zones, an oxygen (02) sensor may be used to detect the 02 content of the ambient air, and ensure that the 02 is at or above a safe level for normal breathing. For example, with 20.9% 02 in normal ambient air, a lower alarm may be set at approximately 19.5%.

In inert work zones, an oxygen sensor may be used to detect the 02 content of the ambient air, and ensure that the 02 is at or below a safe level for inert operations. An example of an inert work zone may be a contained area, such as a pipe or tank, where welding or other similar work may be completed in the inert work zone. To avoid fires and or explosions that may be caused by the work, the 02 may be kept near 0%. As an example, for inert operations, an upper alarm may be set at approximately 4%.

For users that work in both normal operation zones and inert zones, detectors that are set for normal operation may alarm while the user is in the inert zone. Similarly, detectors that are set for inert operations may alarm while the user is in the normal operation zones. This may result in the user having to switch the detector(s) between off/on, carry more than one detector, deal with unnecessary alarms, and other inconveniences and annoyances.

Embodiments of the disclosure include a gas detector, and methods of operating the gas detector, configured to detect when the gas detector is being operated in a normal operation zone or an inert zone. The gas detector may generate acknowledgement requests for the user when the gas detector determines that a different zone has been entered. Additionally, the gas detector may be configured to change alarm settings based on the current zone.

Referring now to FIG. 1, an exemplary system 100 comprising at least one gas detector 102 is shown. The gas detector 102 may be carried by a user while they are working in a normal operation zone 120. While working in the normal operation zone 120, it may be important to ensure that the 02 level in the atmosphere is above a certain level for safe breathing for the user. The 02 sensor 104 may continuously detect the percentage level of 02 in the ambient air. The 02 sensor 104 may be configured to communicate that information to a processor 106, wherein the processor 106 may receive, process, and further communicate the sensed data. In some embodiments, the gas detector 102 may comprise a display 108, wherein the processor 106 may send current sensed data to the display 108 to be communicated to the user. In some embodiments, the gas detector 102 may comprise an alarm 110, wherein the processor 106 may trigger the alarm 110 if the sensed data is below a predefined threshold for safe breathing. In some embodiments, the threshold may be approximately 19.5°/i 02 in the ambient air.

In some embodiments, the gas detector 102 may comprise a user interface 112 configured to receive inputs from a user. The user interface 112 may comprise one or more buttons, touch screens, switches, microphones, displays, screens, lights, indicators, speakers, other similar interfaces, and/or a combination thereof. In some embodiments, the display 108 may be considered to be a part of the user interface 112.

Figure 2:
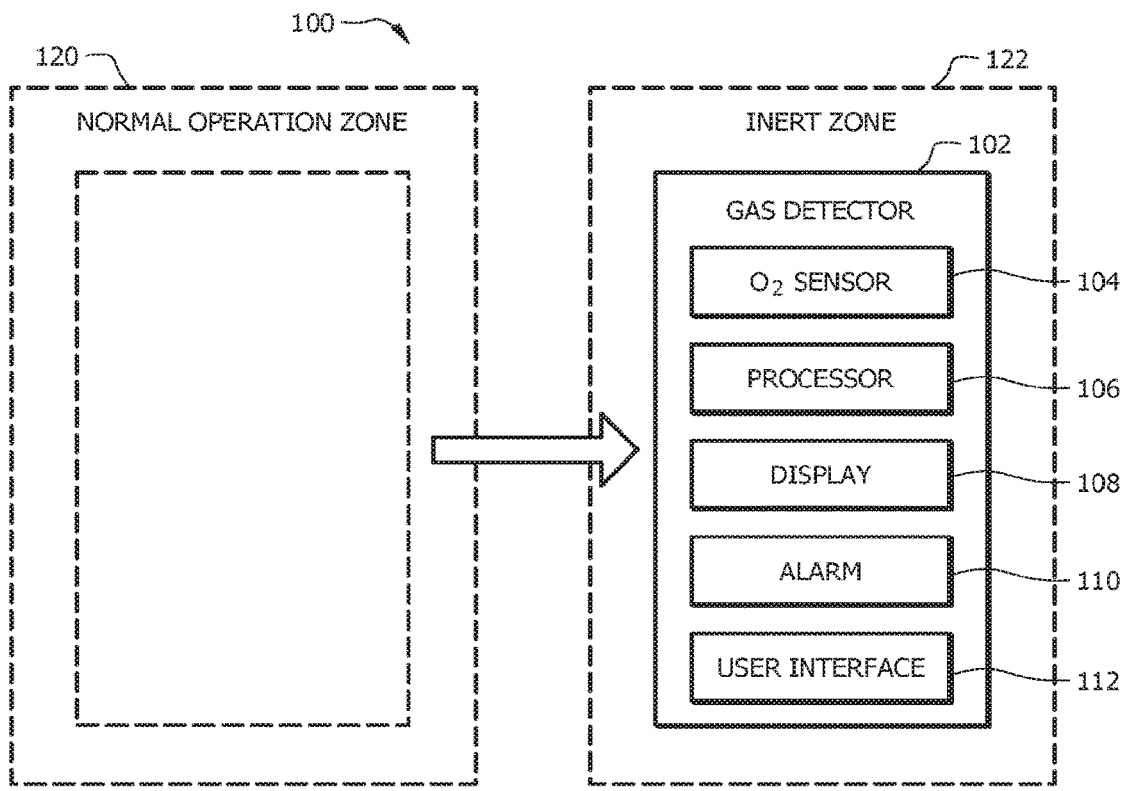
FIG. 2 illustrates a gas detector in use in an inert zone according to an embodiment of the disclosure.

Referring to FIG. 2, in some working environments, a user may need to complete work in an inert environment (or zone) 122. For example, for welding or other similar operations, it may be desired to complete the operation in a low oxygen zone (or inert zone) to avoid fires or explosions that could be caused by the operation. When a user enters an inert zone 122 from a normal operation zone 120, the 02 content in the air may drop from normal breathing levels to inert levels. Typical gas detectors may initiate an alarm based on the drop in 02 in the ambient air, and may continue alarming while the user is in the inert zone 122.

To avoid an unnecessary alarm from the gas detector 102, the gas detector 102 may be configured to recognize when the gas detector 102 has entered an inert zone 122. For example, when the gas detector 102 enters an inert zone 122, the 02 sensor 104 may indicate that the 02 level has dropped below a first predefined threshold for alarm. The processor 106 may receive the sensed data and activate the alarm 110. In some embodiments, the first predefined threshold may be approximately 19.5% 02. In some embodiments, the processor 106 may issue an acknowledgment request to the user, which may be shown via the display 108, to acknowledge if the gas detector 102 has entered an inert zone 122.

In an embodiment, the user may respond to the acknowledgment request indicating that the gas detector has not entered an inert work zone 122, possibly by interacting with the user interface 112. In this case, the alarm 110 may continue to be activated. In some embodiments, when the 02 level rises above the predefined threshold, the alarm 110 may be deactivated, indicating that the ambient air is back within safe breathing range.

In an embodiment, the user may respond to the acknowledgment request indicating that the gas detector has entered an inert work zone 122, possibly by interacting with the user interface 112. When the processor 106 receives this response, the processor 106 may deactivate the alarm 110. Additionally, the processor 106 may change the alarm settings of the gas detector 102 from a first alarm setting to a second alarm setting.

In this example, the first alarm setting may comprise a normal operation mode, and the second alarm setting may comprise an inert operation mode. The first alarm setting may comprise the first predefined threshold, and may indicate that the alarm should be activated when the 02 content is below the first predefined threshold. The second alarm setting may comprise a second predefined threshold, which may be lower than the first predefined threshold. Additionally, the second alarm setting may indicate that the alarm should be activated when the 02 content is above the second predefined threshold.

After the processor 110 has changed the alarm settings, the gas detector may continue operating in the inert operation mode. If the 02 sensor 104 indicates that the 02 level has risen above the second predefined threshold for alarm, the processor 106 may receive the sensed data and activate the alarm 110. In some embodiments, the second predefined threshold may be approximately 4% 02. In some embodiments, the processor 106 may issue an acknowledgment request to the user, which may be shown via the display 108, to acknowledge if the gas detector 102 has left the inert zone 122 and entered the normal operation zone 120 (as shown in FIG. 1).

In an embodiment, the user may respond to the acknowledgment request indicating that the gas detector has not entered the normal operation zone 120, possibly by interacting with the user interface 112. In this case, the alarm 110 may continue to be activated. In some embodiments, when the 02 level lowers below the predefined threshold, the alarm 110 may be deactivated, indicating that the ambient air is back within safe inert range.

In an embodiment, the user may respond to the acknowledgment request indicating that the gas detector has entered the normal operation zone 120, possibly by interacting with the user interface 112. When the processor 106 receives this response, the processor 106 may deactivate the alarm 110. Additionally, the processor 106 may change the alarm settings of the gas detector 102 from the second alarm setting to the first alarm setting.

In another embodiment, the gas detector 102 may comprise alarm settings that contain both the first threshold and the second threshold. The alarm 110 may be activated if the 02 content is between the two thresholds, but it may be deactivated once it is outside of the range, either above or below. Additionally, the mode of operation may be automatically switched from normal operation mode to inert mode, and vice versa.

However, it may be important to receive an acknowledgment from the user before deactivating the alarm, to ensure the safety of the user, and avoid deactivating a legitimate alarm.

In some embodiments, the acknowledgment message may not be issued until the 02 content is outside the range of the two thresholds. For example, when the 02 content drops below 19.5%, the alarm may be activated. Then, if the 02 content continues to drop, when the 02 content drops below 4%, the acknowledgement request may be sent to the user asking if the user has entered an inert zone 122. Similarly, when the 02 content rises above 4%, the alarm may be activated. Then, if the 02 content continues to rise, when the 02 content rises above 19.5%, the acknowledgement request may be sent to the user asking if the user has entered a normal operation zone 120.

In some embodiments, the display 108 may comprise a plurality of colors, wherein different colors may indicate the operation mode (normal or inert) in which the gas detector is currently operating. In some embodiments, another type of display or indicator may be employed to indicate the operation mode (normal or inert) in which the gas detector is currently operating.

In some embodiments, the user may also carry and/or wear respiratory equipment while working in the inert zone 122 and optionally the normal operation zone 120.

In some embodiments, the alarm may comprise one or more multiple step warnings, alarms, and/or alerts comprising different levels of indication. For example, while operating in inert mode, a warning may be activated if the 02 content is above 4%, and an alarm may be activated if the 02 content is above 6%. Similarly, while operating in normal operation mode, a warning may be activated if the 02 content is below 19.5%, and an alarm may be activated if the 02 content is below 18.5%. Additionally, other similar alarm systems may be used by the gas detector 102.

In a first embodiment, a method for gas detection may comprise operating a gas detector with a first alarm setting comprising a first predefined threshold; receiving sensed data containing the current oxygen content in the ambient air; when the sensed data is below the first predefined threshold, activating an alarm; and generating an acknowledgement request for the user asking if the gas detector has entered an inert work zone.

A. second embodiment can include the method of the first embodiment, further comprising displaying the acknowledgment request via a display of the gas detector.

A third embodiment can include the method of the first or second embodiments, further comprising receiving a response from the user indicating that the gas detector has not entered an inert work zone; and continuing to activate the alarm.

A fourth embodiment can include the method of any of the first to third embodiments, wherein the first alarm setting comprises a normal operation mode.

A fifth embodiment can include the method of any of the first to fourth embodiments, wherein the first alarm setting indicates that the alarm is activated when the oxygen content is below the first predefined threshold.

A sixth embodiment can include the method of any of the first to fifth embodiments, further comprising receiving a response from the user acknowledging that the gas detector has entered an inert work zone; deactivating the alarm; changing the alarm settings of the gas detector to a second alarm setting comprising a second predefined threshold; continuing to receive sensed data containing the current oxygen content in the ambient air; when the sensed data is above the second predefined threshold, activating an alarm; and generating an acknowledgement request for the user asking if the gas detector has entered a normal operation work zone.

A seventh embodiment can include method of the sixth embodiment, wherein the second alarm setting comprises an inert operation mode.

An eighth embodiment can include the method of the sixth or seventh embodiments, wherein the second alarm setting indicates that the alarm is activated when the oxygen content is above the second predefined threshold.

A ninth embodiment can include the method of any of the sixth to eighth embodiments, further comprising receiving a response from the user acknowledging that the gas detector has entered a normal operation work zone; deactivating the alarm; changing the alarm settings of the gas detector to the first alarm setting comprising the first predefined threshold; and continuing to receive sensed data containing the current oxygen content in the ambient air.

A tenth embodiment can include the method of any of the sixth to ninth embodiments, further comprising receiving a response from the user indicating that the gas detector has not entered a normal operation work zone; and continuing to activate the alarm.

In an eleventh embodiment, a gas detector may comprise a user interface configured to communicate information to a user, and to receive information from a user; an alarm; a sensor configured to detect the oxygen content in the ambient air around the gas detector; a processor configured to operate the gas detector with a first alarm setting comprising a first predefined threshold; receive sensed data, from the sensor, containing the current oxygen content in the ambient air; when the sensed data is below the first predefined threshold, activate the alarm; and generate an acknowledgement request for the user asking if the gas detector has entered an inert work zone.

A twelfth embodiment can include the gas detector of the eleventh embodiment, wherein the processor is further configured to display the acknowledgment request via the user interface of the gas detector.

A thirteenth embodiment can include the gas detector of the eleventh or twelfth embodiments, wherein the processor is further configured to receive a response from the user, via the user interface, indicating that the gas detector has not entered an inert work zone; and continuing to activate the alarm.

A fourteenth embodiment can include the gas detector of any of the eleventh to thirteenth embodiments, wherein the first alarm setting indicates that the alarm is activated when the oxygen content is below the first predefined threshold.

A fifteenth embodiment can include the gas detector of any of the eleventh to fourteenth embodiments, wherein the processor is further configured to receive a response from the user, via the user interface, acknowledging that the gas detector has entered an inert work zone; deactivate the alarm; change the alarm settings of the gas detector to a second alarm setting comprising a second predefined threshold; continue to receive sensed data, from the sensor, containing the current oxygen content in the ambient air; when the sensed data is above the second predefined threshold, activate an alarm; and generate an acknowledgement request for the user asking if the gas detector has entered a normal operation work zone.

A sixteenth embodiment can include the method of the fifteenth embodiment, wherein the second alarm setting indicates that the alarm is activated when the oxygen content is above the second predefined threshold.

A seventeenth embodiment can include the method of the fifteenth or sixteenth embodiments, wherein the processor is further configured to receive a response from the user, via the user interface, acknowledging that the gas detector has entered a normal operation work zone; deactivate the alarm; change the alarm settings of the gas detector to the first alarm setting comprising the first predefined threshold; and continue to receive sensed data containing the current oxygen content in the ambient air.

An eighteenth embodiment can include the method of any of the fifteenth to seventeenth embodiments, wherein the processor is further configured to receive a response from the user, via the user interface, indicating that the gas detector has not entered a normal operation work zone; and continue to activate the alarm.

In a nineteenth embodiment, a method for gas detection may comprise operating a gas detector with a first alarm setting comprising a first predefined threshold, wherein the first alarm setting indicates that the alarm is activated when the oxygen content is below the first predefined threshold; receiving sensed data containing the current oxygen content in the ambient air; when the sensed data is below the first predefined threshold, activating an alarm; generating an acknowledgement request for the user asking if the gas detector has entered an inert work zone; receiving a response from the user acknowledging that the gas detector has entered an inert work zone; deactivating the alarm; changing the alarm settings of the gas detector to a second alarm setting comprising a second predefined threshold, wherein the second alarm setting indicates that the alarm is activated when the oxygen content is above the second predefined threshold; continuing to receive sensed data containing the current oxygen content in the ambient air; when the sensed data is above the second predefined threshold, activating an alarm; and generating an acknowledgement request for the user asking if the gas detector has entered a normal operation work zone.

A twentieth embodiment can include the gas detector system of the nineteenth embodiment, further comprising receiving a response from the user acknowledging that the gas detector has entered a normal operation work zone; deactivating the alarm; changing the alarm settings of the gas detector to the first alarm setting comprising the first predefined threshold; and continuing to receive sensed data containing the current oxygen content in the ambient air.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F. R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a. limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of" Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for gas detection comprising:
receiving, by a gas detector, sensed data indicative of oxygen content in the ambient air, the gas detector having a first alarm setting comprising a first predefined threshold;
when the sensed data is below the first predefined threshold, activating, by the gas detector, an alarm;
determining when the gas detector enters an inert work zone; and
when the gas detector has entered the inert work zone, deactivating the alarm and altering one or more settings of the gas detector, wherein altering the one or more settings of the gas detector comprises changing the first predefined threshold to a second predefined threshold, and the gas detector is configured to activate the alarm when the sensed data is above the second predefined threshold.

2. The method of claim 1, further comprising:
determining when the gas detector enters the inert work zone based on an input from a user.

3. The method of claim 2, wherein the input is received from the user through a user interface, and wherein the user interface comprises one or more of: buttons, touch screens, switches, microphones, displays, screens, lights, indicators, speakers, or other similar interfaces.

4. The method of claim 2, further comprising:
generating an acknowledgement request for the user asking if the gas detector has entered the inert work zone; and
displaying the acknowledgment request via a display of the gas detector.

5. The method of claim 4, further comprising:
receiving a response from the user indicating that the gas detector has not entered the inert work zone; and
continuing to activate the alarm.

6. The method of claim 1, wherein the first alarm setting indicates that the alarm is activated when the oxygen content is below the first predefined threshold.

7. The method of claim 4, further comprising:
receiving a response from the user acknowledging that the gas detector has entered the inert work zone;
deactivating the alarm;
changing the alarm settings of the gas detector to a second alarm setting comprising the second predefined threshold;
continuing to receive the sensed data indicative of the oxygen content in the ambient air; and
generating an acknowledgement request for the user asking if the gas detector has entered a normal operation work zone.

8. The method of claim 7, wherein the second alarm setting indicates that the alarm is activated when the oxygen content is above the second predefined threshold.

9. The method of claim 7, further comprising:
receiving a response from the user acknowledging that the gas detector has entered the normal operation work zone;
deactivating the alarm;
changing the alarm settings of the gas detector to the first alarm setting comprising the first predefined threshold; and
continuing to receive the sensed data.

10. The method of claim 7, further comprising:
receiving a response from the user indicating that the gas detector has not entered the normal operation work zone; and
continuing to activate the alarm.

11. A gas detector comprising:
a user interface configured to communicate information to a user, and to receive information from a user;
an alarm;
a sensor configured to detect the oxygen content in the ambient air around the gas detector; and
a processor configured to:
receive sensed data indicative of oxygen content in the ambient air, the gas detector having a first alarm setting comprising a first predefined threshold;
when the sensed data is below the first predefined threshold, activate the alarm;
determine when the gas detector enters an inert work zone; and
when the gas detector has entered the inert work zone, deactivate the alarm and altering one or more settings of the gas detector, wherein altering the one or more settings of the gas detector comprises changing the first predefined threshold to a second predefined threshold, and the gas detector is configured to activate the alarm when the sensed data is above the second predefined threshold.

12. The gas detector of claim 11, wherein the processor is further configured to:
determine when the gas detector enters the inert work zone based on an input from a user.

13. The gas detector of claim 12, wherein the input is received from the user through a user interface, and wherein the user interface comprises one or more of: buttons, touch screens, switches, microphones, displays, screens, lights, indicators, speakers, or other similar interfaces.

14. The gas detector of claim 12, wherein the processor is further configured to:
generate an acknowledgement request for the user asking if the gas detector has entered the inert work zone; and
display the acknowledgment request via a display of the gas detector.

15. The gas detector of claim 14, wherein the processor is further configured to:
receive a response from the user indicating that the gas detector has not entered the inert work zone; and
continue to activate the alarm.

16. The gas detector of claim 11, wherein the first alarm setting indicates that the alarm is activated when the oxygen content is below the first predefined threshold.

17. The gas detector of claim 14, wherein the processor is further configured to:
receive a response from the user acknowledging that the gas detector has entered the inert work zone;
deactivate the alarm;
change the alarm settings of the gas detector to a second alarm setting comprising the second predefined threshold;
continue to receive the sensed data indicative of the oxygen content in the ambient air; and
generate an acknowledgement request for the user asking if the gas detector has entered a normal operation work zone.

18. The gas detector of claim 17, wherein the second alarm setting indicates that the alarm is activated when the oxygen content is above the second predefined threshold.

19. The gas detector of claim 17, wherein the processor is further configured to:
receive a response from the user acknowledging that the gas detector has entered the normal operation work zone;

deactivate the alarm;
change the alarm settings of the gas detector to the first alarm setting comprising the first predefined threshold; and
continue to receive the sensed data.

20. The gas detector of claim 17, wherein the processor is further configured to:
receive a response from the user indicating that the gas detector has not entered the normal operation work zone; and
continue to activate the alarm.

* * * * *